(12) United States Patent
Hawkes

(10) Patent No.: US 7,993,380 B2
(45) Date of Patent: Aug. 9, 2011

(54) ACTIVE COMPRESSION ORTHOPEDIC PLATE SYSTEM AND METHOD FOR USING THE SAME

(75) Inventor: David T. Hawkes, Pleasant Grove, UT (US)

(73) Assignee: Alphatel Spine, Inc., Carlsbad, CA (US)

( * ) Notice: Subject to any disclaimer, the term of this patent is extended or adjusted under 35 U.S.C. 154(b) by 705 days.

(21) Appl. No.: 11/394,260

(22) Filed: Mar. 30, 2006

(65) Prior Publication Data

US 2006/0235405 A1    Oct. 19, 2006

Related U.S. Application Data

(60) Provisional application No. 60/667,314, filed on Mar. 31, 2005.

(51) Int. Cl.
*A61B 17/80* (2006.01)

(52) U.S. Cl. .......................... 606/282; 606/299

(58) Field of Classification Search ............... 606/70, 606/71, 74, 86 R, 103, 280–299, 902–906; 623/17.15; 411/411
See application file for complete search history.

(56) References Cited

U.S. PATENT DOCUMENTS

| | | | |
|---|---|---|---|
| 3,900,025 A * | 8/1975 | Barnes, Jr. ................ 606/71 |
| 4,899,543 A | 2/1990 | Romanelli et al. |
| 5,108,398 A | 4/1992 | McQueen et al. |
| 5,616,142 A * | 4/1997 | Yuan et al. ................. 606/71 |
| 5,620,443 A * | 4/1997 | Gertzbein et al. .......... 606/252 |
| 5,713,900 A * | 2/1998 | Benzel et al. .............. 606/250 |
| 5,766,218 A * | 6/1998 | Arnott ....................... 606/151 |
| 5,843,082 A | 12/1998 | Yuan et al. |
| 6,117,135 A * | 9/2000 | Schlapfer ................... 606/250 |
| 6,136,002 A * | 10/2000 | Shih et al. ................. 606/250 |
| 6,342,055 B1 * | 1/2002 | Eisermann et al. ........ 623/17.16 |
| 6,616,666 B1 | 9/2003 | Michelson |
| 6,916,320 B2 | 7/2005 | Michelson |
| 7,008,426 B2 | 3/2006 | Paul |
| 7,479,143 B2 * | 1/2009 | Suh et al. ................... 606/71 |
| 2003/0060828 A1 * | 3/2003 | Michelson ................. 606/71 |
| 2003/0216739 A1 | 11/2003 | Ip et al. |
| 2004/0039388 A1 * | 2/2004 | Biedermann et al. ....... 606/71 |
| 2004/0092939 A1 | 5/2004 | Freid et al. |
| 2004/0116931 A1 * | 6/2004 | Carlson ...................... 606/70 |
| 2004/0147928 A1 * | 7/2004 | Landry et al. .............. 606/61 |
| 2004/0260306 A1 | 12/2004 | Fallin et al. |
| 2005/0004573 A1 * | 1/2005 | Abdou ........................ 606/61 |
| 2005/0043732 A1 * | 2/2005 | Dalton ........................ 606/61 |
| 2005/0203513 A1 * | 9/2005 | Jahng et al. ................. 606/61 |
| 2006/0058796 A1 * | 3/2006 | Hartdegen et al. ......... 606/69 |

* cited by examiner

*Primary Examiner* — Thomas C Barrett
*Assistant Examiner* — Larry E. Waggle, Jr.
(74) *Attorney, Agent, or Firm* — Michael R. Shevlin

(57) ABSTRACT

An active compression orthopedic plate includes a first and a second end cross member, at least one center cross member, at least one longitudinal member slideably coupling the first and second end cross member and the at least one center cross member, and a compressive member configured to exert a compressive force on the first and second end cross members.

21 Claims, 13 Drawing Sheets

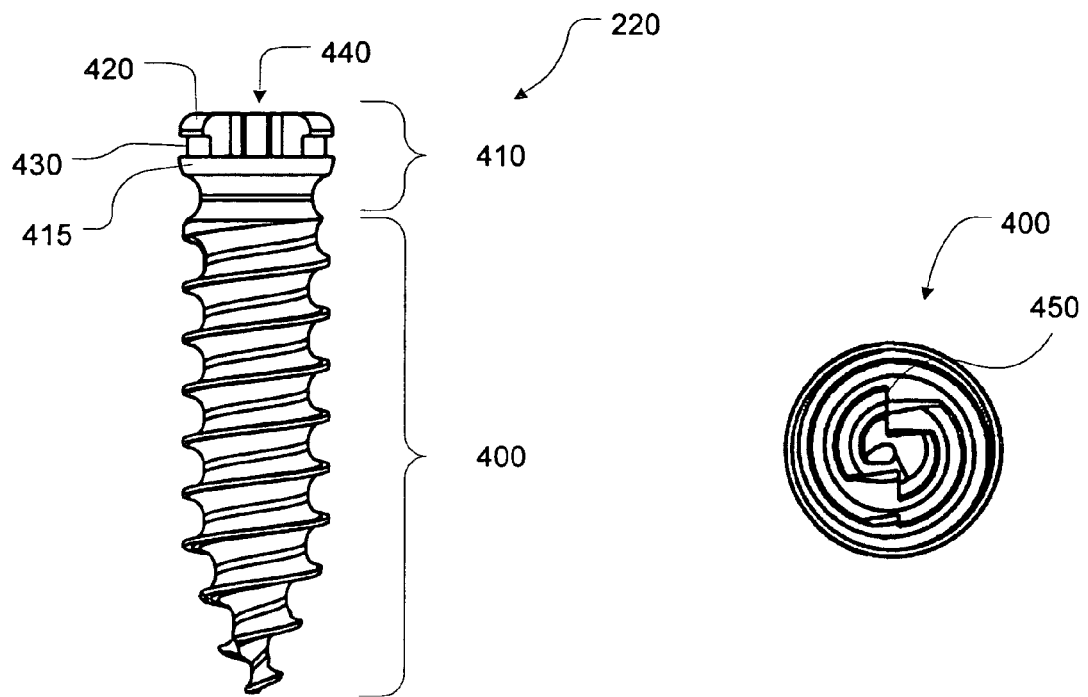
Fig. 4A
Fig. 4B
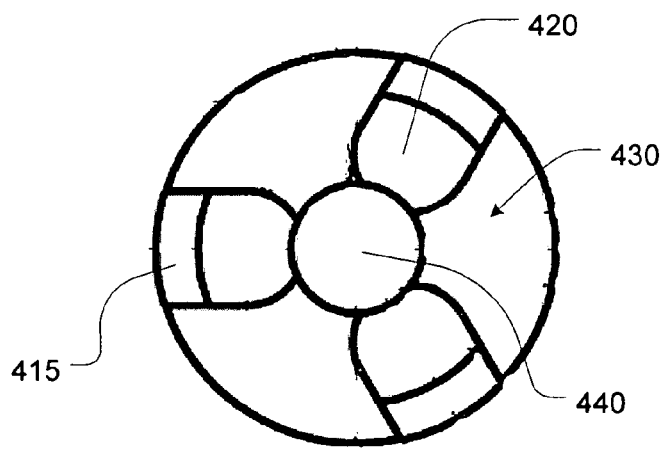
Fig. 4C
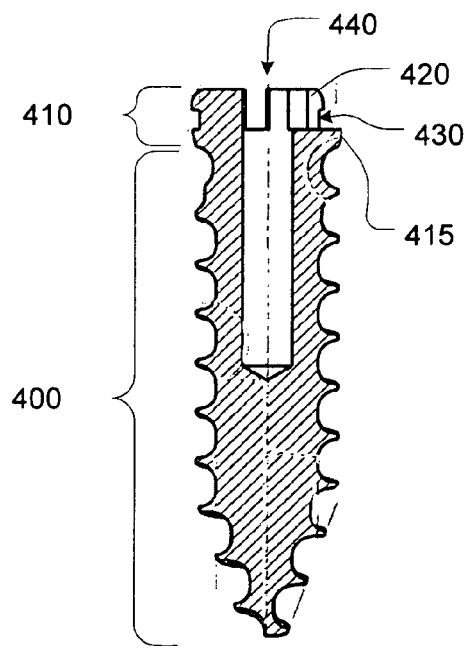
Fig. 4D

ACTIVE COMPRESSION ORTHOPEDIC PLATE SYSTEM AND METHOD FOR USING THE SAME

RELATED APPLICATIONS

This application claims the benefit under 35 U.S.C. §119 (e) of U.S. Provisional Patent Application No. 60/667,314 filed Mar. 31, 2005 titled "Active Compression Cervical Plate." The provisional application is incorporated herein by reference in its entirety.

FIELD

The present system and method relate to bone fixation devices. More particularly, the present system and method provide for an active compression orthopedic plate system.

BACKGROUND

In the treatment of various spinal conditions, including the treatment of fractures, tumors, and degenerative conditions, it is necessary to secure and stabilize the anterior column of the spine following removal of a vertebral body or part. Various devices for internal fixation of bone segments in the human or animal body are known in the art.

Following such removal made using a thoracotomy, thoracoabdominal, retroperitoneal, or similar approach, the normal anatomy is reconstructed using tricortical iliac crest or fibular strut grafts. Not only are removals performed on the thoracic spine, as is the case for the above procedures, but also the cervical spine. Once bone matter is removed, it is then necessary to secure and stabilize the graft, desirably in such a manner as to permit rapid mobilization of the patient. Such objectives can be accomplished by a bone plate. However, to accomplish this service in the optimum manner, it is necessary that the plate be reasonably congruent with the bone to which it is applied, that it have as low a profile as possible, that it be firmly secured to the spinal column so that it is not torn out when the patient places weight and stress upon it and that it be capable of placement and fixation in a manner that is convenient for the surgeon.

In this context it is necessary to secure the plate to the spinal body and also, in some cases, to the graft. After the insertion of a graft and a plate, the graft placed in the patient tends to subside. Traditional cervical plates are designed to limit motion within the fusion mass. However, a German doctor by the surname of Wolff demonstrated that bone grows when in compression and reabsorbs in the absence thereof. Consequently, the latest cervical plate technology has attempted to limit motion of the coupled spinal areas in all directions but compression; theorizing that the natural weight of the head would provide sufficient load to stimulate bone growth in the fusion mass. However, current studies are showing that the cervical plate technology of natural or 'passive' compression is not increasing fusion rates.

SUMMARY

According to one exemplary embodiment, an orthopedic bone fixation device for actively compressing a plurality of bone segments includes a first and a second end cross member, at least one center cross member, at least one longitudinal member slideably coupling the first and second end cross member and the at least one center cross member, and a compressive member configured to exert a compressive force on the first and second end cross members.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

FIGS. 4A-4D show respectively a side, a bottom, a top, and a cross-sectional view of a bone screw, according to one exemplary embodiment.

Figure 1:
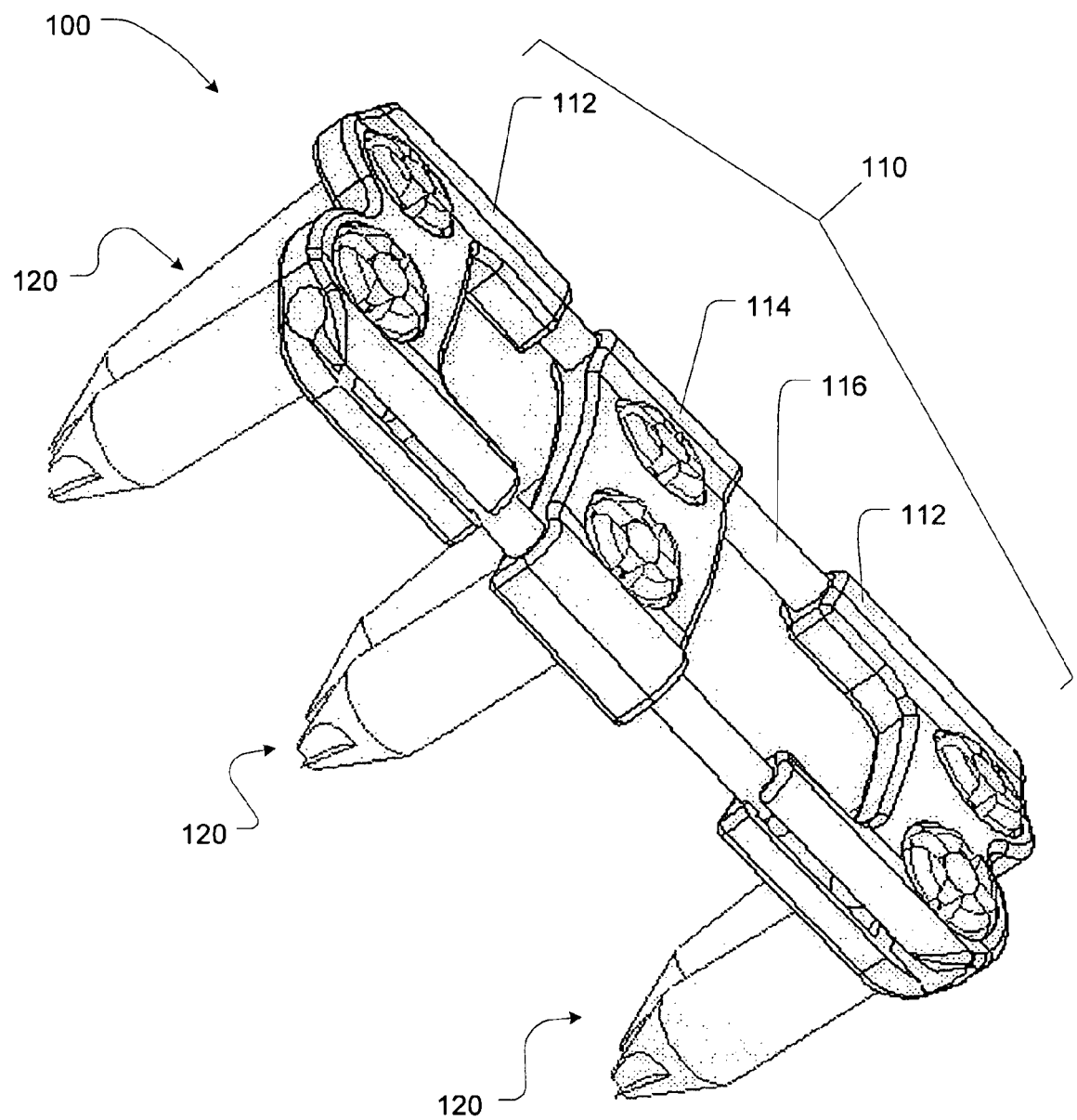
FIG. 1 is a perspective view of an assembled active compression orthopedic plate system, according to one exemplary embodiment.

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Throughout the drawings, identical reference numbers designate similar but not necessarily identical elements.

DETAILED DESCRIPTION

The present specification describes a system and a method for providing an orthopedic plate system that actively compresses attached bone segments. Particularly, according to one exemplary embodiment, the present specification describes the structure of an orthopedic plate system that can be pre-loaded to be in a tensioned state prior to attachment to an orthopedic site. Further details of the present exemplary system and method will be provided below.

While the present exemplary active compression orthopedic plate system may be applied to any orthopedic site, the plate system will be described herein, for ease of explanation only, in the context of a cervical plate application. By way of example, orthopedic plate systems may be used in the treatment of various spinal conditions. As mentioned, when applied to stabilize the position of cervical vertebrae, the plate portion of the orthopedic plate system is designed to lie near and posterior to the esophagus of the patient. Due to its relative location to the esophagus and other connective tissue, the top surface of the plate portion may be smooth and free of sharp corners to prevent irritation or piercing of the esophagus and surrounding tissue. Further, in order to prevent irritation and/or piercing, any connection hardware that is used to couple the plate portion to the cervical vertebrae should remain below or even with the top surface of the plate portion.

Consequently, the present exemplary system and method provide an orthopedic plate system including a bone plate with thru-bores having varying diameters, with the larger diameter being constrained on the top and the bottom by smaller bore diameters. Further, a screw system is described below that, when assembled, is configured to leverage the varying bore diameter of the thru-bores formed in the bone plate to prevent the screw system from backing out.

As mentioned previously, after the insertion of a graft and a plate, the graft placed in the patient tends to subside. Traditional cervical plates are designed to limit motion within the fusion mass. However, bone grows when in compression and resorbs in the absence thereof. Consequently, the present exemplary system and method provides an orthopedic plate configured to provide an "active" compressive force on the fusion mass. As used herein, the term "active" shall be interpreted as referring to a plate configured to provide a compressive force; rather than a "passive" plate which would allow a compressive force but not itself provide a compressive force.

In the following description, certain specific details are set forth in order to provide a thorough understanding of various embodiments of the present active compression orthopedic plate system and method. However, one skilled in the relevant art will recognize that the present exemplary system and method may be practiced without one or more of these specific details, or with other methods, components, materials, etc. In other instances, well-known structures associated with orthopedic plate systems have not been shown or described in detail to avoid unnecessarily obscuring descriptions of the present exemplary embodiments.

As used in the present specification, and in the appended claims, the term "ring" or "expansion ring" shall not be interpreted as necessitating a circular cross section. Rather, as used herein and in the appended claims, the term "ring" or "expansion ring" may include any object having a substantially closed periphery regardless of the cross-sectional profile. The term "ring" shall include objects having flat sided profiles, curvilinear profiles, and/or profiles defined by a varying radius.

Additionally the term "pin" shall be interpreted broadly to include any elongate member, and is not limited to cylindrical elongate members. Rather, as used herein and in the appended claims, the term "pin" shall apply to elongate members having a circular, a quadratic, and/or non-symmetric cross-sectional profile.

Further, as used herein, the term "wire" shall be interpreted to include any number of square, round, or oblong members configured to store energy. Specifically, a wire, when used in the present specification or the appended claims, includes any ligament whether a single member or a plurality of intertwined ligaments.

Unless the context requires otherwise, throughout the specification and claims which follow, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

FIG. 1 illustrates an assembled active compression orthopedic plate system (100), according to one exemplary embodiment. As illustrated, the exemplary active compression orthopedic plate system (100) includes a number of components including, but in no way limited to, a bone plate (110) and at least one screw assembly (120) coupled to the bone plate (110). According to the exemplary embodiment illustrated in FIG. 1, the screw assemblies (120) are configured to be securely coupled to a patient's bone(s) while securely coupling to the bone plate (110) to provide structural and positional stability while preventing issues with the screw assembly backing out.

Further, as illustrated in FIG. 1, the bone plate (110) includes a number of components configured to provide an active compression on a selected fusion mass. As shown, the exemplary bone plate includes, but is in no way limited to, a plurality of end cross members (112) with a center cross member (114) disposed there between. As illustrated, a number of longitudinal members (116) slideably couple the end cross members (112) to the center cross member (114). By way of example only, an exemplary active compression orthopedic plate system may also include a first and second end cross member (112) without a center cross member (114) there between. According to this exemplary embodiment, the active compression may be provided between the first and second end cross members.

Figure 2:
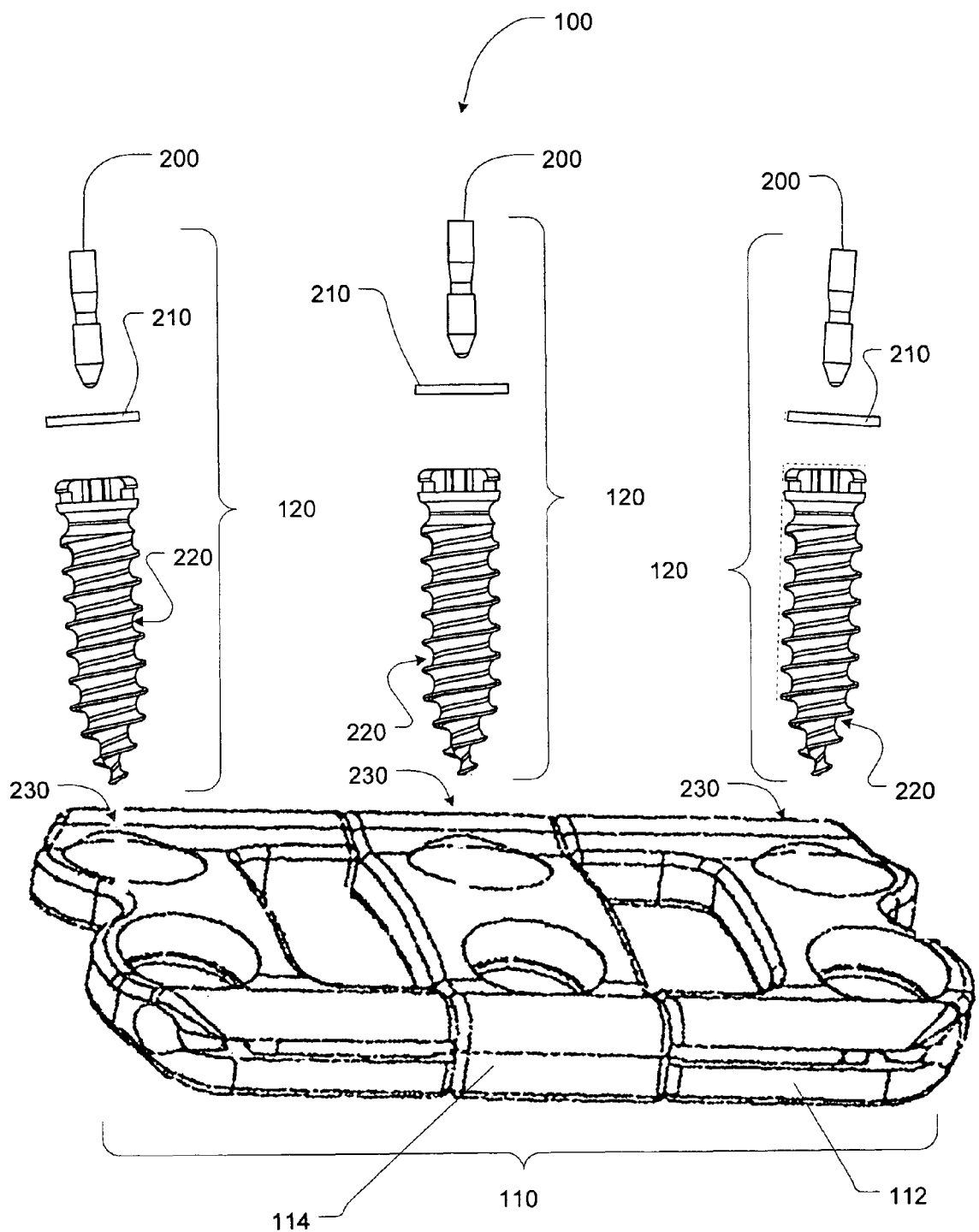
FIG. 2 is a partially exploded view illustrating the components of the screw assembly and active compression orthopedic bone plate of the exemplary embodiment illustrated in FIG. 1.

FIG. 2 is an exploded view of the exemplary active compression orthopedic plate system (100) illustrating the components of one exemplary screw assembly (120). As shown in FIG. 2, the exemplary screw assembly (120) includes, but is in no way limited to, a lock pin (200), an expandable ring (210), and a bone screw (220). While the present exemplary active compression orthopedic plate system (100) is described as including the illustrated exemplary screw assembly (120) to prevent back out of the screw, the orthopedic plate system and method described herein may incorporate any number of fixation means. According to the embodiment shown in FIG. 2, the various portions of the screw assembly (120) are selectively inserted into the thru bore(s) (230) formed in the exemplary bone plate (110). As mentioned, when fully engaged, the exemplary orthopedic plate system (100) is able to maintain a relatively low profile while providing structural support and preventing screw back out. A detailed description of each of the components of the exemplary orthopedic plate system (100) is provided below, followed by a description of their interaction during assembly.

Figure 3A:
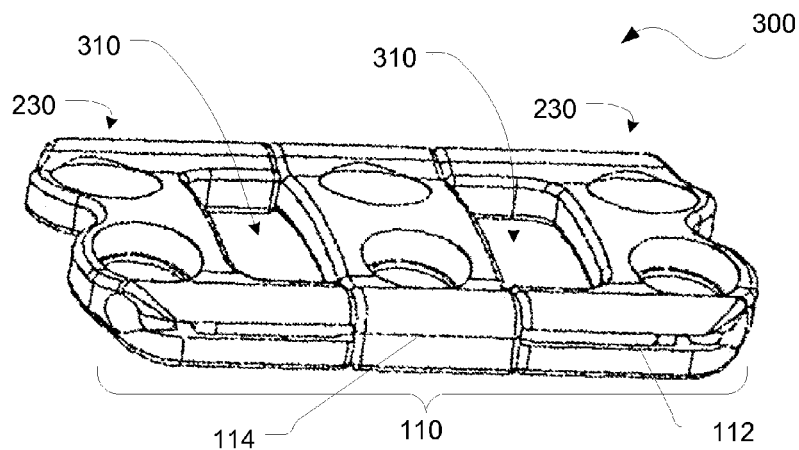
FIGS. 3A-3F illustrate a number of views of various components of the exemplary active compression orthopedic plate system illustrated in FIG. 1, according to various exemplary embodiments.
Figure 3B:
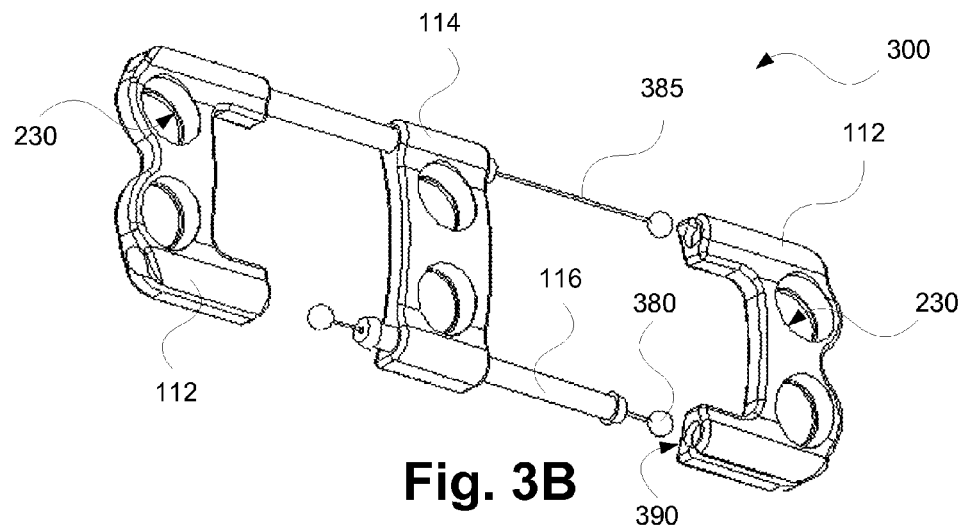

FIGS. 3A through 3F illustrate various views of the bone plate (110) and its exemplary components, according to one exemplary embodiment. As shown, the bone plate (110) generally includes a plurality of end cross members (112). According to one exemplary embodiment, one or more center cross members (114) are disposed between the end cross members (112) to allow connection of the bone plate (110) to three or more locations. As shown in FIGS. 3A through 3D, the end cross members (112) and the center cross member(s) include a plurality of thru-bore(s) (230) formed therein. Additionally, when assembled, the end cross members (112) can be configured to form a number of gaps or material cut-out(s) (310). Further, according to one exemplary embodiment the bone plate (110) assembly is slightly curved to follow the shape of a spinal column and may be formed out of any number of biocompatible metals including, but in no way limited to, stainless steel, titanium, or a titanium alloy. Moreover, the construction of the plate body (300) may be made of non-metal materials including, but in no way limited to, carbon reinforced Polyetheretherketone (PEEK), and the like. Additionally, as illustrated in FIGS. 3A and 3B, the plate body (300) has a beveled rounded periphery to eliminate any sharp or abrupt edges that could potentially be damaging to surrounding tissue.

Figure 9A:
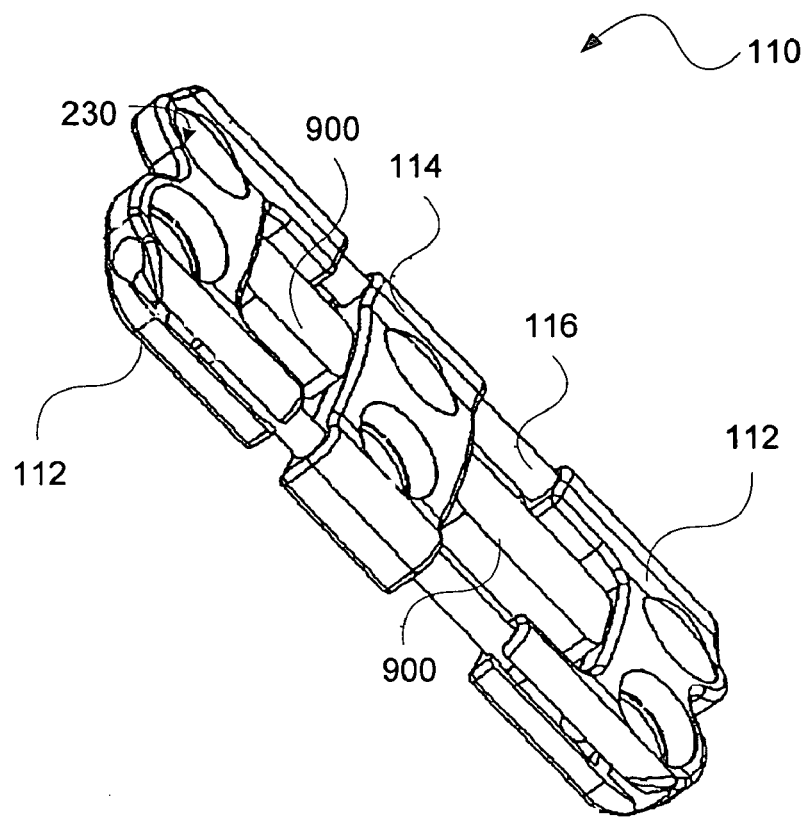
FIGS. 9A and 9B show a perspective view and a top view of an expanded active compression orthopedic plate, respectively, according to one exemplary embodiment.

According to one exemplary embodiment, the material cut-out(s) (310) formed in the plate body (300) may serve a number of purposes. According to one exemplary embodiment, the material cut-out(s) (310) may be designed to eliminate superfluous material, thereby reducing the overall weight of the bone plate (110), while maintaining the desired structural integrity. Additionally, the various material cut-out(s) (310) may be configured to facilitate handling of the bone plate (110) during installation or removal with a tool such as, but in no way limited to, forceps. Further, the material cut-out(s) (310) may also provide functional access to tissue and/or bone located behind an installed bone plate (110) without necessitating removal of the plate. According to one exemplary embodiment, the material cutouts (310) are configured to receive block members (900; FIG. 9A) for holding the bone plate (110) in distraction during installation, as will be described in detail below.

Figure 3C:
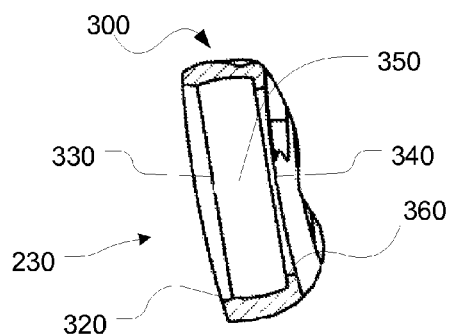

FIG. 3C is a cross-sectional view detailing an exemplary varying profile of the thru-bore(s) (230) formed in the cross members, according to one exemplary embodiment. As shown, a plurality of thru-bores (230) are formed in the cross members, two in each of the end cross members (112) and center cross member(s) (114) of the exemplary embodiment illustrated in FIG. 3A. However, any number of thru-bore configurations may be employed in the cross members to accomplish varying desired coupling points.

As illustrated in the cross-sectional view of FIG. 3C, each of the exemplary thru-bore(s) (230) may include a reception chamfer (320) formed at the interface with the top surface of the plate body (300). The reception chamfer (320) of the exemplary thru bore(s) (230) facilitates reception of a screw assembly (120; FIG. 2) while eliminating the formation of a sharp or potentially damaging edge at the surface of the plate body (300).

Further, as shown, the thru-bore (230) includes a varying bore profile including a top reception diameter (330), a center cavity diameter (350), and an exit diameter (340) defined by a bore stop (360). According to one exemplary embodiment, described in further detail below, both the top reception diameter (330) and the exit diameter (340) of the exemplary thru-bore(s) (230) are smaller than the central cavity diameter (350). Due to the varying bore profile, a screw assembly (120; FIG. 2) having a selectively actuated expansion member may be inserted into the thru-bore(s) (230) and the expansion member actuated to approximately the diameter of the central cavity diameter (350). According to the present exemplary embodiment, expanding the expansion member to approximately the diameter of the central cavity diameter (350) will create an interference fit between the plate body (300) and the expansion member in all directions, thereby eliminating any degrees of freedom the screw assembly (120; FIG. 2) may have relative to the plate body (300). According to another exemplary embodiment, the expansion member may be actuated to a size slightly greater than that of the reception diameter (330) yet less than the central cavity diameter (350). According to this exemplary embodiment, the size of the expansion member will prevent exit of the screw assembly (120; FIG. 1) from the thru-bore (320) while allowing for movement of the screw head within the thru-bore. This movement may be beneficial as an intermediate step when a surgeon is initially placing the bone plate.

Further, according to one exemplary embodiment, the bore stop protrusion (360) that defines the exit diameter (340) of the thru-bore (230) may cause the exit diameter to be smaller than the diameter of the head base (415; FIG. 4) of the screw assembly (120). Consequently, the screw assembly (120) may be inserted into a bone via the bone plate (110) until the head base (415; FIG. 4) is seated upon the bore stop (360). The incorporation of the bore stop provides for consistent insertion of the screw assembly (120) relative to the top surface of the bone plate (110). While the bore profile of the present exemplary thru-bore (230) is illustrated as having gradual changes in the internal diameter, abrupt or dramatic variations in profile of the thru-bore (230) may also define the thru-bore, according to one exemplary embodiment. While the present exemplary active compression orthopedic plate system (100) is described as including the above-mentioned thru-bore system to prevent back out of the screw system (120), any number of comparable systems may alternatively be incorporated with the present orthopedic plate system.

Returning to FIG. 3B, the end cross members (112), and the center cross member (114), are slideably connected by one or more longitudinal members (116). According to the exemplary embodiment illustrated in FIG. 3B, two longitudinal members (116) are used to slideably connect a plurality of end cross members (112) and a single center cross member (114). However, any number of longitudinal members (116) may be used to slideably couple the cross members. As illustrated in FIG. 3B, the exemplary longitudinal members (116) are received by each cross member (112, 114) in an inner guide channel (390). According to one exemplary embodiment the inner guide channels (390) formed in each of the end cross members (112) and the center cross member (114) are sized to receive the longitudinal member. In one exemplary embodiment, the inner guide channels (390) formed in the center cross member (114) are slightly larger than the outer diameter of the longitudinal members (116) to allow the center cross member to be slideably translated on the longitudinal members. Allowing the center cross member(s) (114) to freely float between the end cross members (112) allows the present exemplary bone plate (110) to compensate for any variation in gap distances between vertebral bodies. Further, any number of protruding features (not shown) may, according to one exemplary embodiment, be formed on the walls of the inner guide channels (390) to selectively resist motion or removal of the longitudinal member(s) from the inner guide channels.

Figure 3D:
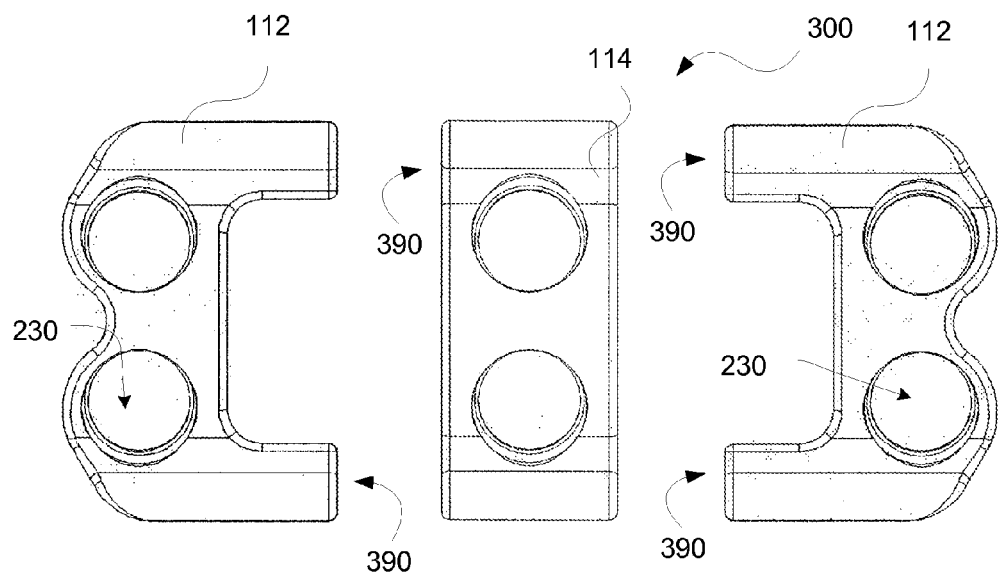
Figure 3E:
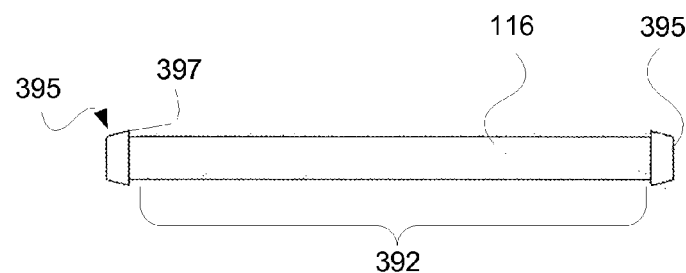

FIG. 3E illustrates a longitudinal member (116), according to one exemplary embodiment. As shown, the exemplary longitudinal member (116) includes a main shaft (392) having a substantially constant cross section, and an expansion stop (395) formed on each end of the main shaft. As illustrated in FIG. 3E, the expansion stops (395) have a barb structure including an increasing diameter terminating abruptly down to the diameter of the main shaft (392). According to one exemplary embodiment, the increasing diameter provides an inclined plane for ease of initial insertion of the longitudinal member in an inner guide channel (390). Further, the face (397) formed by the rapid reduction to the diameter of the main shaft (392) acts as an interference stop between the expansion stop (395) and the exiting orifice of the inner guide channel (390), as will be described in further detail with reference to FIG. 8C. While the exemplary longitudinal member (116) illustrated in FIG. 3E is shown as a substantially cylindrical member, the longitudinal member (116) may assume any number of cross-sectional shapes.

Figure 3F:
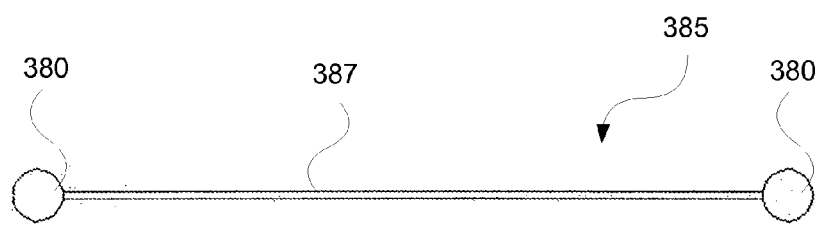

Returning again to FIG. 3B, a super-elastic member (385) configured to provide a compressive force to the present exemplary active compression orthopedic plate system (100) is concentrically placed within the body of the longitudinal member (116). According to the exemplary embodiment illustrated in FIG. 3B, a lumen is formed in the center of the longitudinal member (116) to allow placement of the super-elastic member (385) therein. FIG. 3F illustrates a structure of the super-elastic member (385), according to one exemplary embodiment. As illustrated, the exemplary super elastic member (385) disposed within the longitudinal member (118) may include a wire member (387) with a wire stop member (380) formed on each end.

According to the exemplary embodiment illustrated in FIG. 3B, the super-elastic member (385) is disposed within the longitudinal member (116). However, the super-elastic member (385) may be disposed in any portion of the exemplary bone plate (110) structure, compressibly coupling the two end cross members (112). Additionally, as illustrated in FIG. 3B, two super-elastic members (385) may be included in the exemplary structure. Alternatively, any number of super-elastic members (385) may be used to provide an active compression force on the exemplary orthopedic plate system (100).

According to one exemplary embodiment in which the super-elastic member (385) is disposed within the longitudinal member (116), the wire stops (380) may be coupled to each end of the wire member (387) after being coupled to the longitudinal member. While the exemplary wire member (387) may be formed of any number of elastic materials, the present exemplary wire member is made, according to one exemplary embodiment, of a super-elastic material.

Figure 3G:
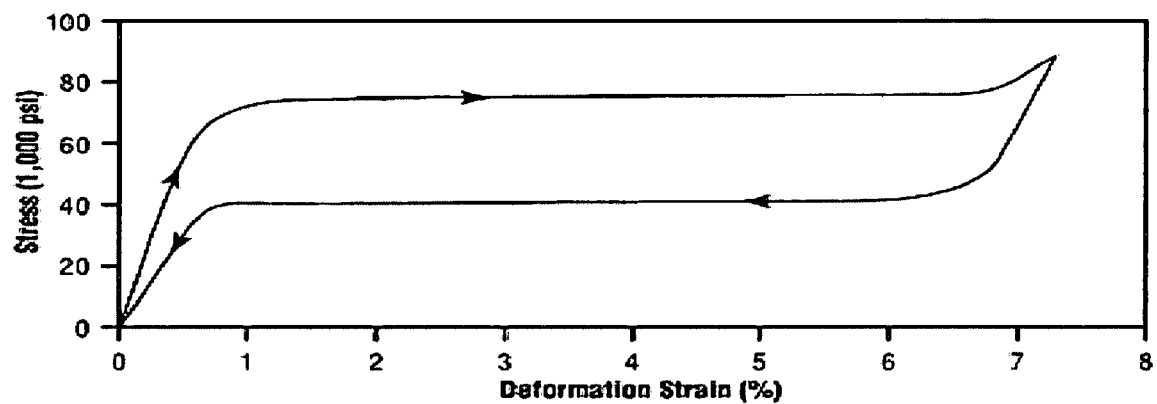
FIG. 3G is a stress/strain diagram illustrating the properties of a super-elastic wire, according to one exemplary embodiment.

The super-elastic material used to form the exemplary wire member (387) may be a shape memory alloy (SMA), according to one exemplary embodiment. Super-elasticity is a unique property of SMA. If the SMA is deformed at a temperature slightly above its transition temperature, it quickly returns to its original shape. This super-elastic effect is caused by the stress-induced formation of some martensite above its normal temperature. Because it has been formed above its normal temperature, the martensite reverts immediately to undeformed austenite as soon as the stress is removed. FIG. 3G is a stress/strain diagram illustrating the properties of a super-elastic material used for the exemplary wire member (387), according to one exemplary embodiment. As shown, an initial increase in deformation strain creates great stresses in the material, followed by a stress plateau with the continued introduction of strain. As the strain is reduced, the stress again plateaus, providing a substantially constant level of stress. This property of the super-elastic material allows the exemplary wire member (387) to be preloaded with compressive forces once inserted in the longitudinal member (116).

According to one exemplary embodiment, the super-elastic material used to form the wire member (387) includes, but is in no way limited to a shape memory alloy of nickel and titanium commonly referred to as nitinol. The wire member (387) may be formed of nitinol, according to one exemplary embodiment, because nitinol wire provides a low constant force at human body temperature. The transition temperature of nitinol wires are made so that they generate force at the temperature of about 37° C. (98.6° F.). Additionally, nitinol exhibits a reduction in elongation at a rate of approximately 10%, which is approximately equal to the subsidence rate of an orthopedic body.

FIGS. 4A through 4D detail a number of elements of a bone screw (220), according to one exemplary embodiment. As illustrated, the bone screw (220) includes features generally classified as a thread portion (400) and a head portion (410). According to one exemplary embodiment, the thread portion (400) of the bone screw (220) is configured to be affixed to the bone of a patient during spine surgery. Particularly, as shown, the thread portion (400) of the exemplary bone screw (220) may include a self-tapping leading edge (450), as is best shown in FIG. 4B. According to this exemplary embodiment, the incorporation of a self-tapping leading edge in the thread portion (400) of the bone screw (220) provides the bone screw with the ability to remove bone material as it is being inserted, eliminating a step of a surgeon drilling a pilot hole prior to insertion of the bone screw.

The head portion (410) of the bone screw (220) includes a number of functional features including, but in no way limited to, a plurality of driving features (420) formed on a head base (415), a ring channel (430) formed in a side of the driving features, and a pin bore (440) extending from the center of the head portion into the center of the thread portion (400). According to the present exemplary embodiment, the head portion (410) of the bone screw (220) transitions from the thread portion (400) with the head base (415). According to one exemplary embodiment, the outer diameter of the head base (415) is larger than the outer diameter of any section of the thread portion (400). By forming the head base (415) larger than the thread portion (400) of the bone screw (220), the thread portion of the bone screw may pass through an appropriately sized thru-bore (230; FIG. 2) substantially corresponding in size with the thread portion while preventing the head base from passing there through. This configuration allows for consistent insertion depth of the bone screw (220) into a desired thru-bore (230; FIG. 2).

A number of protrusions in the form of driving features (420) are formed extending upwardly from the head base (415), according to one exemplary embodiment. As illustrated in FIGS. 4A and 4C, the shown embodiment includes three protrusions acting as driving features (420). However, any number of driving features (420) may be formed on the head base (415), according to the teachings of the present exemplary system and method. According to one exemplary embodiment, at least the upper portion of the driving features may be engaged by a corresponding driving feature during installation. According to this exemplary embodiment, the corresponding driving feature (not shown) may engage the driving features (420) and impart a rotational force thereon, driving the thread portion (400) of the bone screw (220) into a desired bone.

As illustrated in FIGS. 4A and 4D, an annular groove is formed in the driving features (420) to form a ring channel (430) around the head portion (410) just above the head base (415). According to one exemplary embodiment, the ring channel (430) formed in the driving features (420) of the present exemplary bone screw (220) is sufficiently deep to receive and house an expandable ring (210; FIG. 2) in a relaxed state and retain the expandable ring when driven open to retain the screw assembly (120; FIG. 1) in a thru-bore (230; FIG. 2).

A pin bore (440) is also formed in the exemplary bone screw (220), as is best illustrated in FIG. 4D. According to one exemplary embodiment, the pin bore (440) is formed concentric with the axis of the bone screw (220) and has a diameter substantially similar to the diameter of the lock pin (200; FIG. 2). As shown in FIG. 4D, the pin bore (440) may also correspond in height with the height of a lock pin (200; FIG. 2) to assure the lock pin may be fully inserted into the pin bore (440) during operation.

Alternatively, the pin bore (440) formed in the exemplary bone screw (220) may be formed with a height that well exceeds the height of a lock pin (200). According to this alternative embodiment, the bone screw (220) may have a pin bore (440) that extends through the entire screw height. According to this exemplary embodiment, the extended pin bore (440) not only allows for a lock pin (200) to be fully engaged to selectively expand an expandable ring (210), but also allows for a lock pin to be extended beyond the expandable ring into the pin bore (440), thereby facilitating a release of the expandable ring.

Figure 5A:
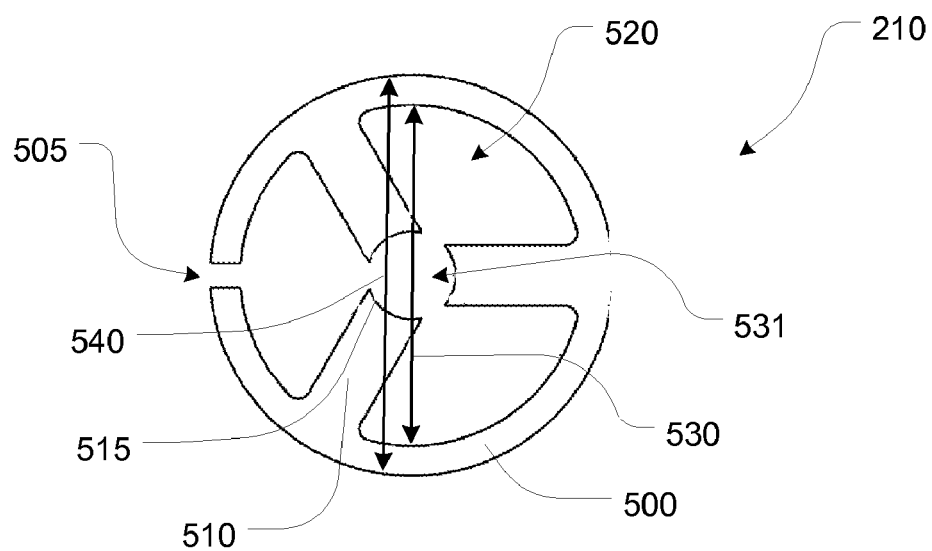
FIGS. 5A and 5B are respectively a top and a side view of an expandable ring configured to be mated with a bone screw, according to one exemplary embodiment.
Figure 5B:
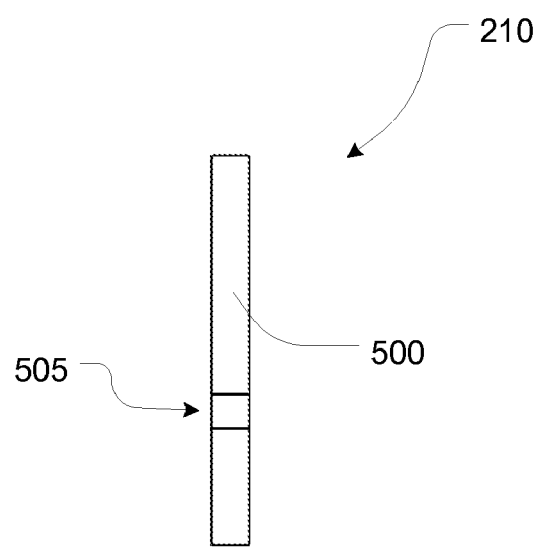

FIGS. 5A and 5B illustrate the expandable ring (210) of the screw assembly (210; FIG. 2), according to one exemplary embodiment. As shown in FIGS. 5A and 5B, the exemplary expandable ring is configured to mate with and be selectively expanded in the ring channel (430; FIG. 4A) of the bone screw (220). Specifically, the expandable ring (210) includes a substantially circular outer rib (500) having an expansion gap (505) formed therein. According to one exemplary embodiment, the expansion gap (505) is configured to facilitate the expansion and contraction of the expandable ring (210) without causing undue stresses on the member material. The width of the outer rib (500) is defined by the difference between the inner diameter (530) of the outer rib and the outer diameter (540) of the outer rib. According to one exemplary embodiment described in further detail below, the difference between the inner diameter (530) and the outer diameter (540) is such that the expandable ring (210) may be retained in the ring channel (430; FIG. 4A) of the bone screw (220; FIG. 2) in both an un-expanded state and an expanded state within a thru-bore (230; FIG. 2).

In addition to the expansion gap (505), the expandable ring (210) includes a number of expansion ribs (510) protruding from the outer rib (500) toward the center of the expandable ring. As shown, the expansion ribs (510) terminate in a lock pin engagement surface (515) and define a driving feature orifice (520) between each pair of adjacent expansion ribs and a pin orifice (531) between the lock pin engagement surfaces. According to one exemplary embodiment, the driving feature orifices (520) are configured to receive the driving features (420; FIG. 4C) formed on the head portion (410; FIG. 4A) of the bone screw (220; FIG. 2), during assembly. Additionally, the lock pin engagement surfaces (515) cause the pin orifice (531) to be concentrically aligned with the pin bore (440; FIG. 4D) when assembled. Consequently, the engagement surfaces are configured to receive a lock pin (200; FIG. 2) and translate any variations in the surface profile of the lock pin to the outer rib (500) as the lock pin is passed into the pin bore (440; FIG. 4D), thereby controlling the expansion and/or contraction of the outer rib (500).

Figure 6A:
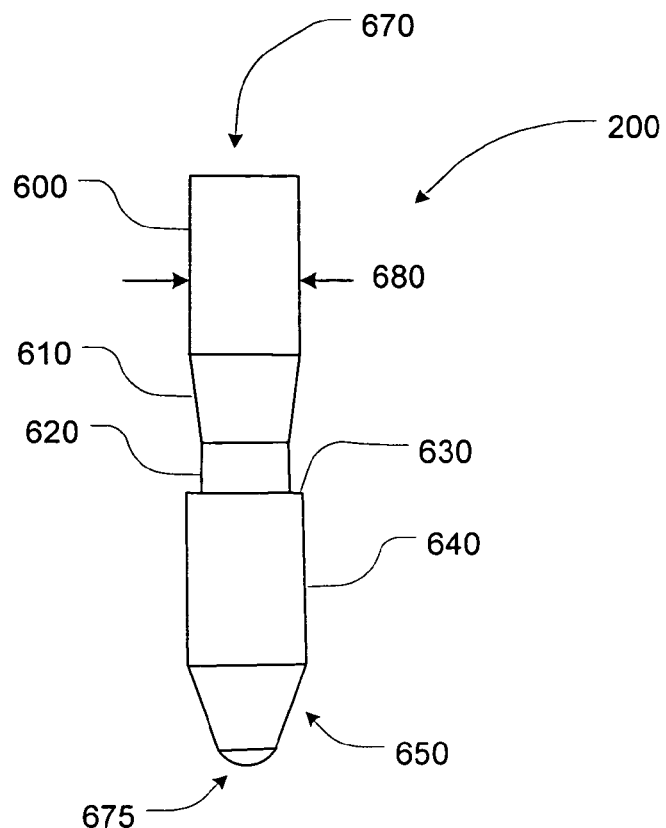
FIGS. 6A and 6B are a side view and a top view of a lock pin, according to one exemplary embodiment.
Figure 6B:
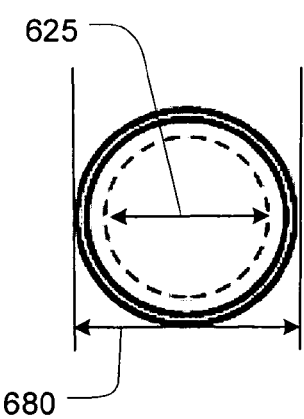

FIGS. 6A and 6B illustrate an exemplary lock pin (200) according to one exemplary embodiment. As shown, the exemplary lock pin (200) is a substantially cylindrical member having a proximal (670) and a distal end (675). Additionally, a number of cut outs and/or tapers are formed in the lock pin (200) to create a varying outer pin diameter (680). According to the exemplary embodiment illustrated in FIGS. 6A and 6B, the lock pin (200) includes an entry taper (650) formed on the distal end (675) thereof. The entry taper (650) is a graduated surface configured to facilitate initial alignment and engagement of the lock pin (200) with both the pin orifice (530; FIG. 5A) of the expandable ring (210; FIG. 5A) and the pin bore (440; FIG. 4D) of the bone screw (220; FIG. 4D).

Moving towards the proximal end (670) of the lock pin (200), the entry taper (650) leads to an entry body (640) having a substantially consistent outer pin diameter (680) configured to at least slightly expand the expandable ring (210) during assembly. The entry body (640) leads to a retention cut-out portion (630) that defines a small diameter surface (620) of the lock pin (200). According to one exemplary embodiment, the small diameter surface (620) has a relaxed diameter (625) substantially corresponding to the pin orifice (530; FIG. 5A) in a relaxed or near relaxed expandable ring state. According to one exemplary embodiment, when the screw assembly (120; FIG. 2) is assembled, the expandable ring (210) engages the small diameter surface (620), allowing the expandable ring to remain in a relaxed state until fully engaged.

Continuing towards the proximal end (670) of the lock pin (200), a graduated expansion surface (610) extends from the small diameter surface (620), terminating in the lock surface (600) portion of the lock pin (200). During a locking step of the present exemplary system, the lock pin (200) is advanced in the pin bore (440; FIG. 4D) such that the lock pin engagement surfaces (515; FIG. 5A) of the expandable ring (210) engage the graduated expansion surface (610) and the lock surface (600) to expand the expandable ring to an appropriate diameter within the thru-bore (230; FIG. 2). According to one exemplary embodiment, the outer pin diameter (680) of the lock surface (600) is sufficient to expand the expandable ring (210; FIG. 2) to a desired friction inducing state, while still constraining the expandable ring in the ring channel (430; FIG. 4A) and without permanently deforming the expansion ring. Further detail of the function and operation of the exemplary active compression orthopedic plate system (100) will be described below with reference to FIGS. 7-11B.

Exemplary Method

Figure 7:
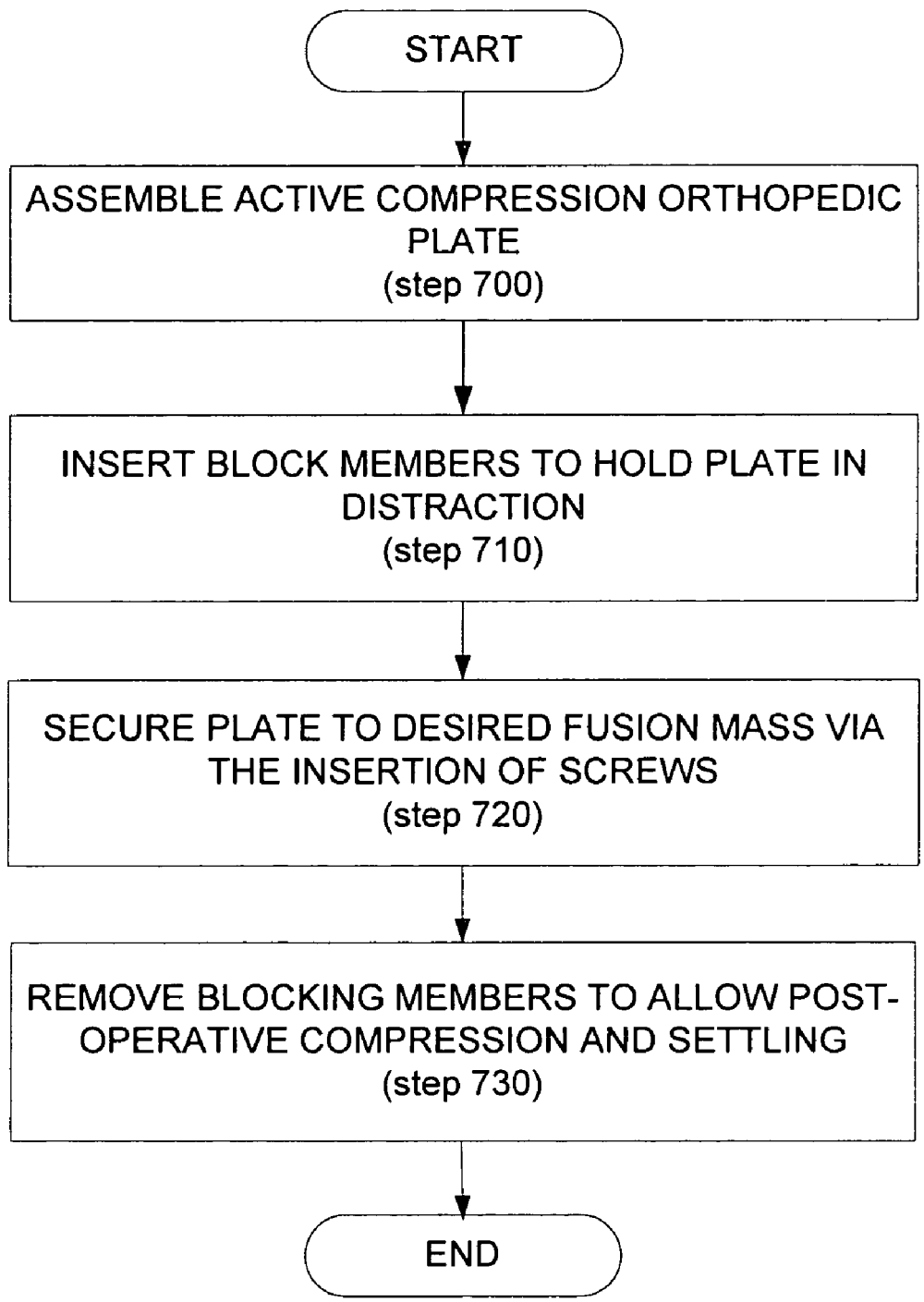
FIG. 7 is a flow chart illustrating a method of securing an active compression orthopedic plate to a number of desired vertebral bodies, according to one exemplary embodiment.

FIG. 7 illustrates a method for installing the active compression orthopedic plate system (100; FIG. 1), according to one exemplary embodiment. As illustrated in FIG. 7, the present exemplary method for installing the active compression orthopedic plate system (100; FIG. 1) includes assembling the active compression orthopedic plate (step 700). Once the active compression orthopedic plate system is appropriately positioned, the orthopedic plate system may be drawn apart and block members placed in the material cutouts to hold the plate in distraction (step 710). The distracted active compression orthopedic plate system is then coupled to a desired fusion mass by inserting screws through the thru-bores into the fusion mass and surrounding bone members (step 720). When secured to the desired fusion mass, the blocking members are removed from the material cutouts, allowing the plate system to actively compress the desired fusion mass during post operative settling (step 730). Further details of each step of the present exemplary method will be provided below with reference to FIGS. 8A through 11B.

Figure 8A:
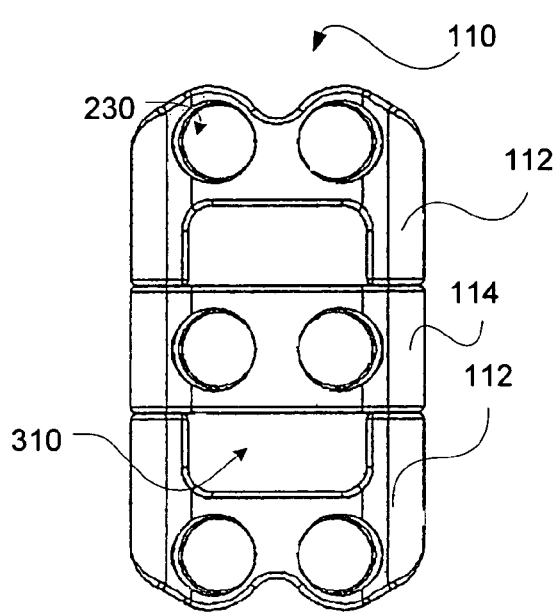
FIGS. 8A through 8C are various views of an assembled active compression orthopedic plate including an enlarged perspective view of an expansion stop in an end cross member, according to one exemplary embodiment.
Figure 8B:
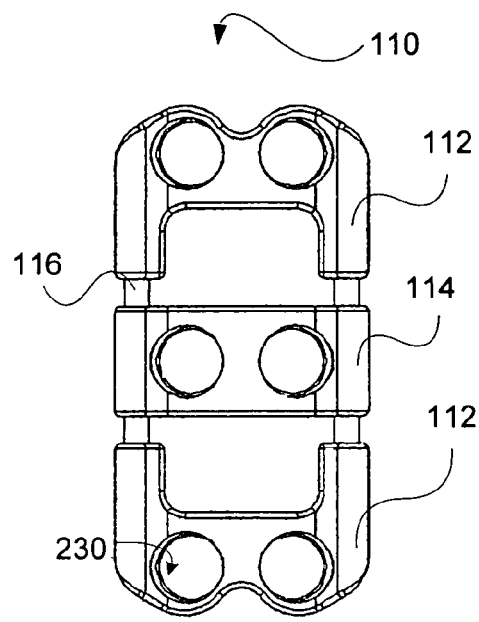
Figure 8C:
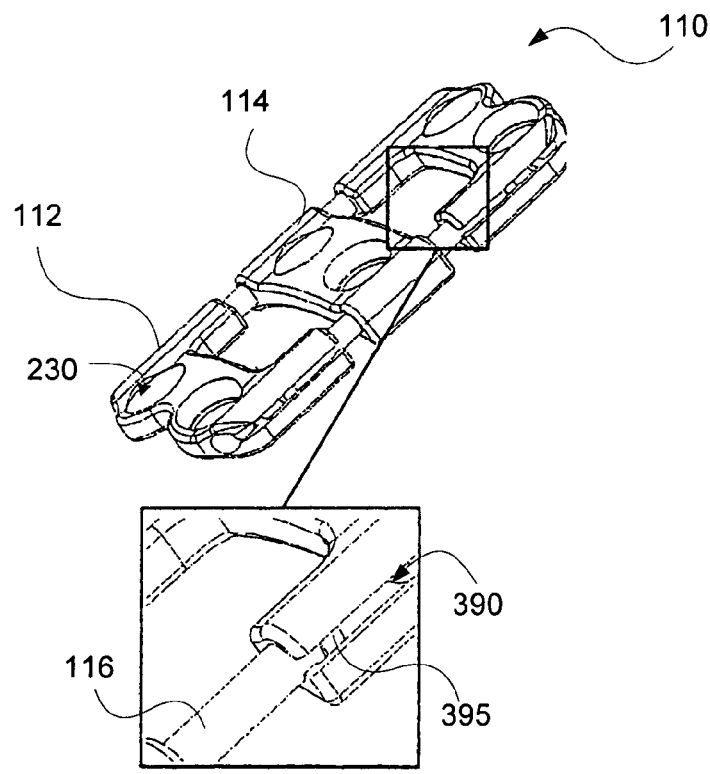

As illustrated in FIG. 7, the first step of the exemplary method is to assemble the exemplary active compression orthopedic plate system (step 700). The present exemplary active compression orthopedic plate system (100; FIG. 1) can be assembled prior to implantation or in-situ. FIGS. 8A through 8C illustrate an assembled orthopedic plate system, according to one exemplary embodiment. As shown in FIG. 8A, the assembled system in its un-disturbed state includes the end cross members (112) immediately adjacent to the center cross member (114). In this exemplary state, the strains introduced on the super-elastic wire member (385; FIG. 3B) are minimized. Further, when assembled, the longitudinal members (116) are disposed within the inner guide channels (390; FIG. 3D) of the end cross members (112) and the center cross member (114). Additionally, the wire stops (380) are independently coupled to the internal portions of the end cross members (112) by any number of mechanisms including, but in no way limited to, adhesives, mechanical fasteners, and/or an interference fit with a protrusion in the inner guide channel (390; FIG. 3D).

Once assembled, the end cross members (112) may be separated relative to one another, thereby introducing super-elastic strain into the super-elastic member (385; FIG. 3F), placing the active compression orthopedic plate system (100; FIG. 1) in a distracted state, illustrated in FIG. 8B. As shown in FIG. 8C, the expansion stop (395) formed on the longitudinal member (116) can engage a protruding member of the inner guide channels (390), preventing the release of the longitudinal member, and inadvertent disassembly of the components.

Figure 9B:
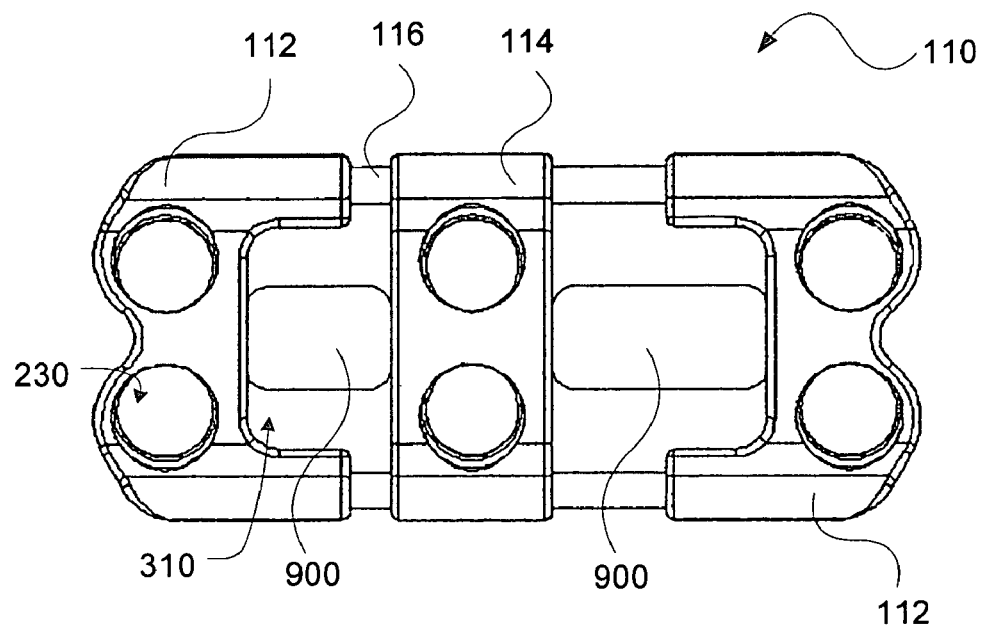

With the active compression orthopedic plate system (100; FIG. 1) in a distracted state, a plurality of block members may be inserted in the material cutouts to hold the plate in distraction (step 710). FIGS. 9A and 9B illustrate the exemplary active compression orthopedic plate system (100; FIG. 1) in a distracted state, with the blocking members (900) maintaining the relative separation between the end cross members (112). According to one exemplary embodiment, the blocking members (900) are used to hold the exemplary plate system (100; FIG. 1) in distraction during screw insertion. Further, as illustrated in FIGS. 9A and 9B, by slideably coupling the center cross member (114) to the longitudinal members (116), the center cross member (114) can be adjusted relative to the end cross members (112). Specifically, as shown in FIGS. 9A and 9B, the blocking members (900) may be of varying sizes, allowing the exemplary active compression orthopedic plate system (100; FIG. 1) to be specifically fitted or customized to the often varying vertebral levels of a patient.

Figure 10A:
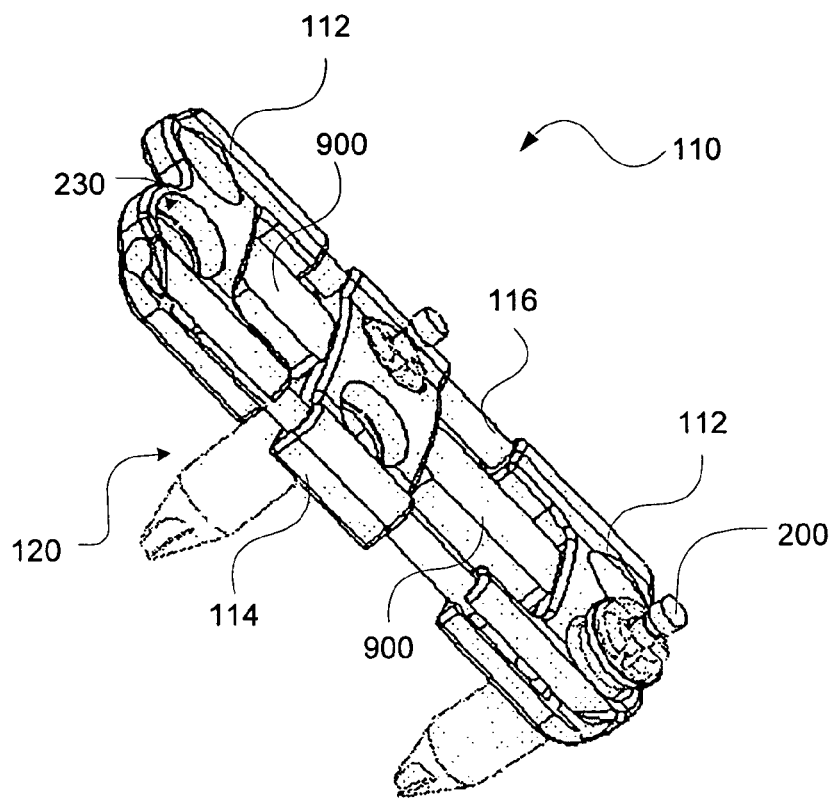
FIGS. 10A and 10B are a perspective view and a top view of an expanded active compression orthopedic plate system including assembled screw systems, in accordance with one exemplary embodiment.
Figure 10B:
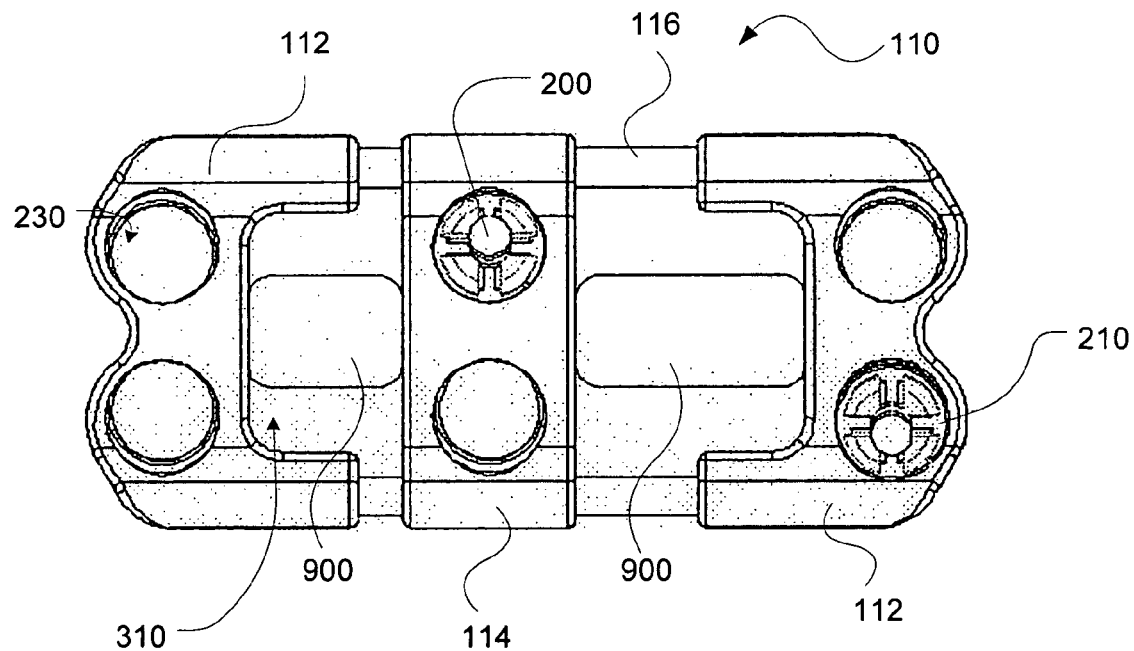

As the active compression plate system is held in distraction (step 710), the bone plate (110) is coupled to a desired fusion mass (step 720). The placement of the bone plate (110; FIG. 1) relative to a vertebral bone in a patient may be pre-operatively determined based on a pre-operative examination of the patient's spinal system using non-invasive imaging techniques known in the art, such as x-ray imaging, magnetic resonance imaging (MRI), and/or fluoroscopy imaging, for example. Any additional preparation or work may be done on and around the desired vertebral bone prior to positionally orienting the distracted bone plate. As illustrated in FIGS. 10A and 10B, the bone plate (110) is oriented such that the reception chamfer (320; FIG. 3C) is facing away from the desired bone, facilitating insertion of the present screw assembly.

With the bone plate appropriately positioned relative to a desired vertebral bone, the screw assemblies (120) can be presented to the thru-bores (230) of the bone plate (110) with the expandable ring in a relaxed state. As shown in FIG. 10A, the lock pin (200) is undeployed and the expandable ring (210) is in a relaxed state. More specifically, according to one exemplary embodiment, the small diameter surface (620; FIG. 6A) of the lock pin (200) is engaged with the lock pin engagement surfaces (515; FIG. 5A) of the expandable ring (210).

When presented, the screw assembly (120) may be driven through the thru-bore (230) in the bone plate (110) into a desired vertebral bone (step 720). As mentioned, the screw assembly may be driven into the desired vertebral bone by coupling a driving tool to the driving features (420) of the bone screw (220). Once mated, the driving tool may impart a rotational force on the head portion (410) of the bone screw (220). Consequently, the self-tapping thread portion (400; FIG. 4A) of the bone screw (220) will remove bone material as it advances into the desired bone. The screw assembly (120) may be partially driven initially if multiple screw assemblies (120) are to be inserted in a single bone plate (110) or if further work is to be done by a surgeon prior to final assembly.

The screw assembly (120) may be driven through the thru-bore (230) until the head portion (410) of the bone screw (220) is within the central cavity of the thru-bore (step 730). As mentioned previously, consistent seating of the screw assembly (120) in the thru-bore (230) may be accomplished by driving the bone screw (220) into the thru-bore (230) until the head base (415; FIG. 4A) of the bone screw seats upon the bore stop (360; FIG. 3C) within the thru-bore. FIGS. 10A and 10B illustrate a number of screw assemblies (120) seated in the thru-bore (230) as described above.

Once the screw assembly is correctly positioned in the thru-bore (230), the lock pin (200) may be engaged to enlarge the diameter of the expandable ring (210), capturing the screw within the thru-bore. As the lock pin (200) is actuated, the expansion ring (210) is acted upon by the varying profile of the lock pin. Specifically, the graduated expansion surface (610; FIG. 6A) of the lock pin (200) will impart an increasing force on the expansion ring (210) until the lock pin is fully engaged and the lock surface (600) is imparting a desired outward force upon the expansion ring. While an axial translation of the lock pin imparts a radial force on the expansion ring of the exemplary embodiment detailed herein, movement of the lock pin is in no way limited to an axial translation. Rather, by way of example, a lock pin having a non-circular cross-sectional profile, such as a triangle or other lobed profile, may be rotated within the pin bore (440) to impart a changing radial force on the expansion ring. In response to the increased outward force exerted by the lock surface (600) of the lock pin (200) upon the expansion ribs (540; FIG. 5A) of the expansion ring (210), the diameter of the expansion ring is enlarged about the head portion (410; FIG. 4A) of the bone screw assembly (120). The enlarging of the expansion ring (210) about the head portion (410; FIG. 4A) of the bone screw assembly (120) imparts an outward force from the expansion ring to the inner surface of the thru-bore (230). According to one exemplary embodiment, the outward force exerted by the expansion ring (210) to the thru-bore (230) creates a frictional fit that captures the bone screw (220) within the thru-bore of the bone plate. Further, as mentioned above, the outer diameter of the expansion ring (210) in its expanded state is larger than both the reception diameter (330; FIG. 3C) and the exit diameter (340; FIG. 3C) of the exemplary thru-bore (230). Consequently, the bone screw assembly (120) is prevented from backing out from, or further advancing in the thru-bore (230).

Figure 11A:
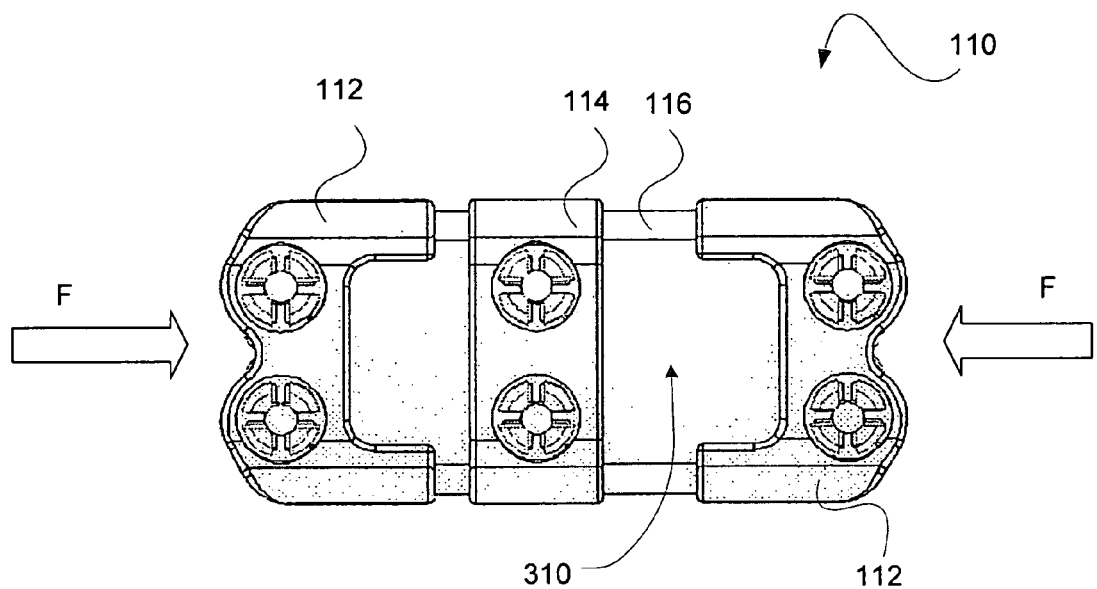
FIGS. 11A and 11B are a top and a perspective view, respectively, of a fully assembled active compression orthopedic plate system, according to one exemplary embodiment.
Figure 11B:
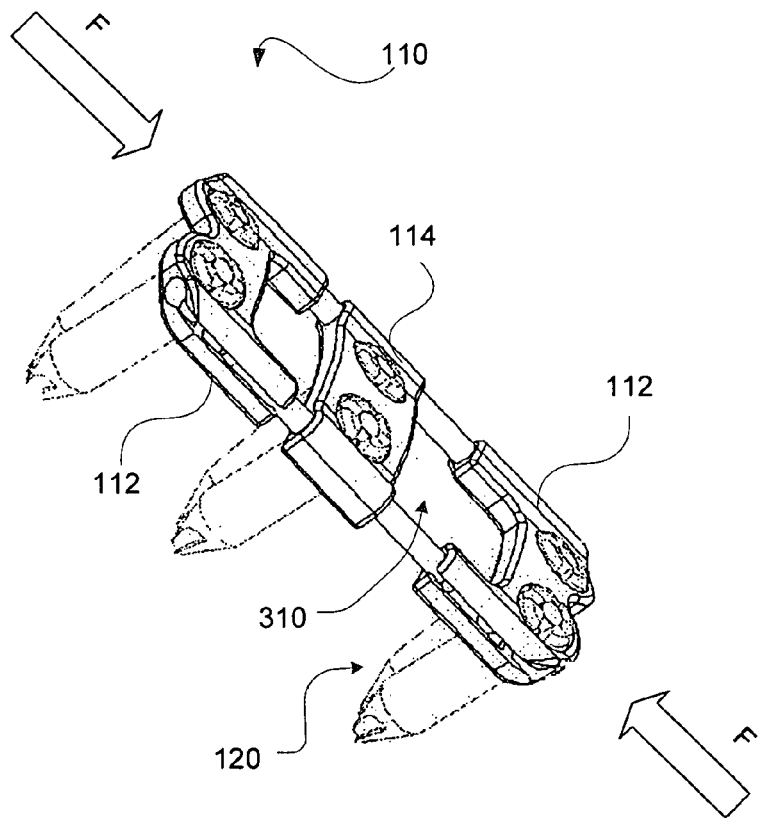

When the exemplary active compression orthopedic plate system (100; FIG. 1) is secured to a desired fusion mass (step 720; FIG. 7), the blocking members are removed to allow post operative compression and settling (step 730; FIG. 7). As shown in FIGS. 11A and 11B, removal of the blocking members allows the end cross members (112) and the center cross member (114) to translate along the longitudinal members (116). According to the present exemplary embodiment, the super-elastic members (385; FIG. 3B) are in super-elastic strain, imparting a force on the bone plate (110), as illustrated by the force arrows (F). This force (F) encourages the motion of the cross members to be towards compression. Post operative settling of the graft is accommodated by the longitudinal members sliding in the plates and the compression of the super-elastic members.

In conclusion, the present exemplary systems and methods provide for an active compression orthopedic plate system. Particularly, the present exemplary system is configured to actively impart a compressive force on a desired fusion mass. Consequently, the present exemplary active compression orthopedic plate system increases osteogenic stimulation as well as fusion graft and spinal segment stabilization.

The preceding description has been presented only to illustrate and describe the present method and system. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the present exemplary system and method be defined by the following claims.

What is claimed is:

1. An active compression orthopedic plate, comprising:
   a first and a second end cross member;
   at least one longitudinal member slideably coupling said first and second end cross members, said at least one longitudinal member being an independent member from said first and second end cross member;
   a compressive member configured to exert a compressive force on said first and said second end cross members; wherein said compressive member comprises an elastic member having a first and second end; and wherein at least one of the first and second ends is removably secured to at least one of the first and second end cross members: and
   wherein said compressive member is at least partially disposed within said at least one longitudinal member.

2. The active compression orthopedic plate of claim 1, further comprising at least one center cross member slideably disposed between said first and second end cross members by said at least one longitudinal member.

3. The active compression orthopedic plate of claim 2, further comprising at least one thru-bore defined in each of said first and second end cross member and said at least one center cross member.

4. The active compression orthopedic plate of claim 3, wherein said thrubore is defined by a central cavity, said central cavity having a middle diameter, an entry diameter, and an exit diameter, said middle diameter being larger than both said entry diameter and said exit diameter.

5. The active compression orthopedic plate of claim 2, further comprising: at least one longitudinal orifice formed in each of said first and second end cross member and said at least one center cross member; said longitudinal orifices configured to receive said at least one longitudinal member.

6. The active compression orthopedic plate of claim 5, wherein said at least one longitudinal member comprises: a main body having a cross-sectional area smaller than a cross sectional area of said longitudinal orifices; and an expansion stop formed on each end of said main body; said expansion stop having a cross-sectional area greater than said main body cross sectional area.

7. The active compression orthopedic plate of claim 1, wherein said elastic member comprises a shape memory alloy.

8. The active compression orthopedic plate of claim 7, wherein said shape memory alloy comprises nitinol.

9. The active compression orthopedic plate of claim 1, wherein said compressive member further comprises: a wire stop member disposed on each end of said compressive member; said wire stop members being configured to be coupled to said first and said second end cross member.

10. The active compression orthopedic plate of claim 1, further comprising a plurality of material cut-outs defined by said first and said second end cross members; and at least one blocking member configured to maintain a position of said first end cross member relative to a second end cross members while said orthopedic plate is distracted.

11. An active compression orthopedic plate, comprising:
    a first and a second end cross member;
    at least one center cross member;
    at least one independent longitudinal member slideably coupling said first and second end cross member and said at least one center cross member;
    a compressive member configured to exert a compressive force on said first and said second end cross members; wherein said compressive member comprises an elastic member having a first and second end; and wherein at least one of the first and second ends is removably secured to at least one of the first and second end cross members; and
    wherein said compressive member is at least partially disposed within a center lumen of said at least one longitudinal member.

12. The active compression orthopedic plate of claim 11, further comprising at least one thru-bore defined in each of said first and second end cross member and said at least one center cross member.

13. The active compression orthopedic plate of claim 12, Wherein said thru-bore is defined by a central cavity, said central cavity having a middle diameter, an entry diameter, and an exit diameter, said middle diameter being larger than both said entry diameter and said exit diameter.

14. The active compression orthopedic plate of claim 11, further comprising: at least one longitudinal orifice formed in each of said first and second end cross member and said at least one center cross member; said longitudinal orifices configured to receive said at least one longitudinal member.

15. The active compression orthopedic plate of claim 14, wherein said at least one longitudinal member comprises: a main body having a cross-sectional area smaller than a cross sectional area of said longitudinal orifices; and an expansion stop formed on each end of said main body; said expansion stop having a cross-sectional area greater than said main body cross sectional area.

16. The active compression orthopedic plate of claim 11, wherein said elastic member comprises a shape memory alloy.

17. The active compression orthopedic plate of claim 16, wherein said shape memory alloy comprises nitinol.

18. An active compression orthopedic plate, comprising:
at least a first, second, and third interconnected cross members having mounting apertures therein; and
at least one longitudinal member interconnecting said cross members, said longitudinal member including a flexible member extending from a first and a second end of said longitudinal member, the flexible member having a first and second end; and wherein at least one of the first and second ends is removably secured to the at least one of the first, second, and third interconnecting cross members, the flexible member also including a securing member disposed on said flexible member, the flexible member under tension;
wherein the first end of the longitudinal member extends through an insert in a side of a first cross member, the longitudinal member extending through a reciprocal sleeve of the second cross member, the second end of the longitudinal member extending through an insert in a side of a third cross member; wherein the cross members are free to translate along the at least one longitudinal members member and are in compression relative to each other.

19. The active compression orthopedic plate of claim 18, wherein said flexible member comprises a shape memory alloy.

20. The active compression orthopedic plate of claim 19, wherein said shape memory alloy comprises nitinol.

21. The active compression orthopedic plate of claim 7, wherein said shape memory alloy comprises:
at least one wire member formed of a shape memory alloy, said at least one wire having a first and a second end;
a wire stop member formed on each of said first and second end of said wire member;
wherein said wire member is configured to be disposed in a lumen defined by said at least one longitudinal member; and wherein said wire stop member is configured to engage said first and second end cross member.

* * * * *

UNITED STATES PATENT AND TRADEMARK OFFICE
CERTIFICATE OF CORRECTION

| | | |
|---|---|---|
| PATENT NO. | : 7,993,380 B2 | Page 1 of 1 |
| APPLICATION NO. | : 11/394260 | |
| DATED | : August 9, 2011 | |
| INVENTOR(S) | : David T. Hawkes | |

It is certified that error appears in the above-identified patent and that said Letters Patent is hereby corrected as shown below:

Title Pg, Item (73) Assignee: Delete "Alphatel" and insert -- Alphatec --.

Signed and Sealed this
Thirteenth Day of March, 2012

David J. Kappos
*Director of the United States Patent and Trademark Office*